US011039809B2

(12) United States Patent
Lemaitre et al.

(10) Patent No.: US 11,039,809 B2
(45) Date of Patent: Jun. 22, 2021

(54) SYSTEM AND METHOD FOR CALIBRATION OF AN X-RAY TUBE

(71) Applicant: GE Precision Healthcare LLC, Wauwatosa, WI (US)

(72) Inventors: Sergio Lemaitre, Milwaukee, WI (US); John Boudry, Waukesha, WI (US); Bradley Gabrielse, Waukesha, WI (US); Ryan Lemminger, Milwaukee, WI (US); Spencer Cutler, Waukesha, WI (US)

(73) Assignee: GE PRECISION HEALTHCARE LLC, Wauwatosa, WI (US)

( * ) Notice: Subject to any disclaimer, the term of this patent is extended or adjusted under 35 U.S.C. 154(b) by 89 days.

(21) Appl. No.: 16/388,948

(22) Filed: Apr. 19, 2019

(65) Prior Publication Data

US 2019/0320994 A1    Oct. 24, 2019

Related U.S. Application Data

(60) Provisional application No. 62/660,349, filed on Apr. 20, 2018.

(51) Int. Cl.
*G01D 18/00* (2006.01)
*A61B 6/00* (2006.01)
(Continued)

(52) U.S. Cl.
CPC .............. *A61B 6/582* (2013.01); *G01T 7/005* (2013.01); *H01J 35/147* (2019.05);
(Continued)

(58) Field of Classification Search
CPC ........... A61B 6/032; A61B 6/40; A61B 6/582; A61B 6/583; A61B 6/08; A61B 6/4021; A61B 6/4291; A61B 6/0421; A61B 6/0487; A61B 6/06; A61B 6/405; A61B 6/482; A61B 6/488; A61B 6/505; A61B 6/548;
(Continued)

(56) References Cited

U.S. PATENT DOCUMENTS

6,339,635 B1 *   1/2002   Schardt ................. H01J 35/305
                                                                378/113
7,409,043 B2     8/2008   Dunham et al.
(Continued)

*Primary Examiner* — Irakli Kiknadze (57) ABSTRACT

A system and method for calibrating an X-ray tube is provided in which the X-ray tube includes an electronic storage medium associated with the X-ray tube on which calibration information for the X-ray tube is stored. The calibration information includes operating parameters for the focusing elements of the X-ray tube for desired focal spots, tolerance limits for variations in the focal spots and a number of gradient coefficient values corresponding to certain modulation transfer functions (MTF) for the X-ray tube that the imaging system can employ in an iterative manner to correct the operating parameters of the focusing elements to achieve the desired focal spot. This automatic iterative process significantly reduces the time required for the calibration of the X-ray tube. The system and method also employs scan sequencing to minimize the heat generated enabling the scans to be completed in a shorter amount of time than prior calibration processes.

19 Claims, 6 Drawing Sheets

(51) Int. Cl.
*G01T 7/00* (2006.01)
*H05G 1/32* (2006.01)
*H01J 35/14* (2006.01)
*H05G 1/52* (2006.01)

(52) U.S. Cl.
CPC ............ *H01J 35/153* (2019.05); *H05G 1/32* (2013.01); *H05G 1/52* (2013.01)

(58) Field of Classification Search
CPC .......... A61B 2562/0219; A61B 6/4405; A61B 6/466; A61B 6/542; A61B 6/547; A61B 6/5205; A61B 6/025; A61B 6/145; A61B 6/4007; A61B 6/4035; A61B 6/425; A61B 6/461; A61B 6/5217; A61B 6/587; A61B 6/035; A61B 6/54; A61B 6/4435; A61B 6/584; A61B 6/5258; A61B 6/4241; A61B 5/0035; A61B 6/037; A61B 6/4085; A61B 6/4417; A61B 6/50; A61B 6/5282; A61B 6/585; A61B 6/4014; A61B 6/4233; A61B 6/4452; A61B 6/5235; G01T 7/005; G01T 1/17; G01T 1/16; G01T 1/169; G01T 1/2985; G01T 1/026; G01T 1/1603; G01T 1/161; G01T 1/1615; G01T 1/1642; G01T 1/1648; H01J 35/147; H01J 35/153; H01J 35/045; H01J 35/06; H01J 35/14; H01J 35/08; H01J 2235/086; H01J 2235/1291; H01J 35/10; H01J 35/12; H01J 35/305; H01J 1/14; H01J 1/15; H01J 29/006; H01J 29/04; H01J 29/484; H01J 29/485; H01J 3/26; H05G 1/32; H05G 1/52; H05G 1/025; H05G 1/28; H05G 1/38; H05G 1/42; H05G 1/44; G01N 23/046; G01N 2223/419; G01N 2223/204; G01N 2223/612; G01N 23/044; G01N 2223/3035; G01N 2223/401; G21K 1/10; G21K 1/025; G21K 1/04; A61N 5/10; G06N 3/0454; G06N 3/084; G06N 20/00; G06T 11/005; G06T 11/008; G06T 2207/10081; G06T 2211/408; G06T 11/006; G06T 11/003; G06T 2207/20081; G06T 2207/20084; G06T 2211/40; G06T 2211/424; G06T 5/50; G06T 2207/20064; G06T 2207/20221; G06T 2207/20224; G06T 2211/436; G06T 5/001; G06T 5/10; G06T 5/20; G06T 2207/10104; G06T 5/007; G06T 2207/30048; G06T 2207/30061; G06T 7/30; G06K 9/00; H01L 27/1446; H01L 27/14603; H01L 27/14658; H01L 27/14812
USPC ................................ 378/119, 137, 138, 207
See application file for complete search history.

(56) References Cited

U.S. PATENT DOCUMENTS

| | | | |
|---|---|---|---|
| 8,265,227 B2 | 9/2012 | Boudry et al. | |
| 8,320,521 B2 * | 11/2012 | Zou | H01J 35/045 378/16 |
| 8,401,151 B2 | 3/2013 | Frontera et al. | |
| 8,712,015 B2 * | 4/2014 | Caiafa | H01J 35/14 378/110 |
| 8,938,050 B2 * | 1/2015 | Lemaitre | H01J 35/06 378/137 |
| 9,048,064 B2 * | 6/2015 | Boye | H01J 35/14 |
| 9,153,409 B2 * | 10/2015 | Wiedmann | H01J 35/14 |
| 2011/0142193 A1 | 6/2011 | Frontera et al. | |

* cited by examiner

SYSTEM AND METHOD FOR CALIBRATION OF AN X-RAY TUBE

CROSS-REFERENCE TO RELATED APPLICATIONS

This application claims priority from U.S. Provisional Patent Application Ser. No. 62/660,349, filed on Apr. 20, 2018, the entirety of which is expressly incorporated herein by reference for all purposes.

BACKGROUND OF THE DISCLOSURE

The disclosure relates generally to diagnostic imaging systems and methods, and more particularly, to a system and method for calibrating an X-ray tube.

X-ray systems typically include an X-ray tube, a detector, and a support structure for the X-ray tube and the detector. In operation, an imaging support, on which an object is positioned, is located between the X-ray tube and the detector. The X-ray tube typically emits radiation, such as X-rays, toward the object. The radiation typically passes through the object on the support and impinges on the detector. As radiation passes through the object, internal structures of the object cause spatial variances in the radiation received at the detector. The detector then emits data received, and the system translates the radiation variances into an image, which may be used to evaluate the internal structure of the object. One skilled in the art will recognize that the object may include, but is not limited to, a patient in a medical imaging procedure or an inanimate object as in, for instance, a package in an X-ray scanner or computed tomography (CT) package scanner.

X-ray tubes include a rotating anode structure for the purpose of distributing the heat generated at a focal spot. The anode is typically rotated by an induction motor having a cylindrical rotor that supports a disc-shaped anode target and a stator structure that surrounds an elongated neck of the X-ray tube. The rotor of the rotating anode assembly is driven by the stator.

An X-ray tube cathode provides an electron beam that is accelerated using a high voltage applied across a cathode-to-anode vacuum gap to produce X-rays upon impact with a target track of the anode. The area where the electron beam impacts the target track is often referred to as the focal spot. Typically, the cathode includes one or more resistive filaments positioned within a cup for providing electron beams to create a high-power, large focal spot or a high-resolution, small focal spot, as examples. Typically, an electrical current is passed through the resistive elements, thus causing the resistive elements to increase in temperature and emit electrons when in a vacuum.

Imaging applications may be designed that include real-time control of focal spot size (length and width) and position on the target track. The position of the focal spot may be kept at the same track location (ignoring track rotation) or dynamically deflected view-by-view between two or three or more positions. In some X-ray tubes, focal spot control is enabled via electrodes surrounding the filament within the cathode structure or via electromagnets in the electron beam drift region. Changes in current (mA) and voltage (kVp) to the cathode filaments affect the position and size of the focal spot.

According to one example, to compensate for current and voltage adjustments, electrode voltages within the cathode are adjusted to achieve a desired or targeted focal spot size and position. According to another example, focal spot size and position may be controlled using magnetic lenses (dipole, quadrupole, multipole) instead of or additional to electrostatic control as described with respect to the electrode voltages. Such adjustments may occur at the start of the scan (dependent upon user selection of mA and kVp) or during an exam (e.g., mA adjustment during the exam). For a modern X-ray tube capable of microsecond X-ray intensity switching, quadrupole magnets are used to control focal spot size. To achieve this the quadrupole currents vary over a range of several amps over the full application range (typically: 70-140 kVp, 10-1300 mA, small to large focal spot sizes). The currents supplied to the magnets are required to be controlled within a few milliamps to achieve proper focal spot size on the target.

Due to manufacturing variability for the components of the X-ray tubes, the values for the focal spot control are typically determined for each X-ray tube and imaging system combination to achieve the targeted focal spot sizes and positions (within a predetermined tolerance) for a plurality of currents and voltages. The values determined for a particular X-ray tube within one imaging system, however, may cause the X-ray tube to exceed focal spot tolerances when the particular X-ray tube is coupled to another generator. For example, values determined using a testing imaging system during a manufacturing process of the X-ray tube may be different from those required for the same X-ray tube within an imaging system into which the X-ray tube is to be installed.

When a new X-ray tube is installed within an imaging system, when another component of the imaging system relating to the X-ray tube is replaced, such as a voltage tank or magnet control board, among others, or in order to evaluate any degradation of performance of an X-ray tube already installed within an imaging system due to aging, calibration of the X-ray tube is required to ensure the required image quality for the imaging system. However, with the fine adjustments required for the proper operation of the X-ray tube to achieve the desired focal spot size, once the X-ray tube is installed within the imaging system a large number of calibration points across the operational ranges for the X-ray tube must be obtained to determine the proper operation of the X-ray tube within the system. These calibration points are then stored within the imaging system for the X-ray tube for later use in determining whether the X-ray tube is within the proper operating parameters during the useful life of the X-ray tube. One example of such a calibration system is disclosed in U.S. Pat. No. 7,409,043, entitled Method and Apparatus to Control Radiation Tube Focal Spot Size, the entirety of which is expressly incorporated by reference herein However, the process for the calibration of the X-ray tube is highly time and effort intensive. In particular, in each of these situations where calibration is necessary, the number of calibration points that need to be determined for proper use of the X-ray tube requires significant time to operate the X-ray tube at each point to obtain the information necessary for the storage within the system for calibration purposes. Further, the calibration information is only utilized to correct for ongoing variations of focal spot size during operation of the X-ray tube, rather than enabling a calibration of the overall functioning of the X-ray tube.

Therefore, it would be desirable to design a system and method capable of efficiently calibrating the overall functionality of an X-ray tube particular to the imaging system into which the X-ray tube is to be or has been installed.

BRIEF DESCRIPTION OF THE DISCLOSURE

In one exemplary embodiment of the present disclosure, a system and method for calibrating an X-ray tube is provided in which the X-ray tube includes an electronic storage medium associated with the X-ray tube on which calibration information for the X-ray tube is stored. The calibration information includes values representing the operating parameters for the focusing elements of the X-ray tube for desired focal spots that are determined during the initial testing of the X-ray tube after manufacture of the X-ray tube, as well as tolerance limits for variations in the focal spots. The stored calibration information also includes a number of gradient or sensitivity coefficient values corresponding to certain focal spot size functions, such as modulation transfer functions (MTF), for the X-ray tube that are employed to correct the operating parameters to achieve the desired focal spot size. This data is stored in a computer-readable format in the electronic storage medium and is accessed by the imaging system during a calibration procedure performed for the X-ray tube. In the procedure, the imaging system can operate the X-ray tube and focusing elements at the operating parameters specified for each of the focal spot sizes. Should a focal spot be determined to be out of the tolerance range(s), the imaging system can employ the gradient or sensitivity coefficients with the MTF in an iterative manner to correct the operating parameters of the focusing elements to achieve the desired focal spot. This automatic iterative process provides the technical effect of significantly reducing the time required for the calibration of the X-ray tube within the imaging system in which it has been installed.

In another exemplary embodiment of the present disclosure, the system and method provides a sequencing algorithm for the scans performed during the calibration process. This sequencing of the scans accommodates the heat generated by each scan in order to minimize the potential of damage being done to the X-ray tube as a result of overheating. The scan sequencing has the technical effect of ordering the scans performed in the calibration process to minimize the heat generated in order to enable the scans to be completed in a shorter amount of time than prior calibration processes and/or by preventing any source protection algorithm from stopping the calibration process prior to its completion.

In one exemplary embodiment of the disclosure, a system for the calibration of an X-ray tube includes an imaging system having a control mechanism, a computer and an electronic storage device operably connected to one another and an X-ray tube connected to the imaging system, wherein the computer is configured to access initial parameters of operation for the X-ray tube at a number of focal spots, the initial parameters including values for X-ray tube voltage, X-ray tube emission, operating currents and linearized focal spot size functions and gradients therefor, determining a calibration state of the X-ray tube, optionally operating the X-ray tube at a first portion of the number of focal spots to determine any offsets for the initial parameters, optionally updating the initial parameters with the offsets, operating the X-ray tube at each of a second portion of the number of focal spots and determining if any of the second portion of focal spots are outside of calibration tolerance limits.

In another exemplary embodiment of the disclosure, a method for the calibration of an X-ray tube includes the steps of providing original parameters of operation for a first number of focal spots, the original parameters including values for X-ray tube voltage, X-ray tube emission, operating currents and linearized focal spot size functions and gradients therefor, operating the X-ray tube at the original parameters, determining values for any offsets in the original parameters and updating the original parameters to provide updated parameters for the first number of focal spots.

In an exemplary embodiment of the method of calibrating an X-ray tube including magnetic focusing elements includes the steps of providing initial parameters of operation for the X-ray tube at a number of focal spots, the initial parameters including values for X-ray tube voltage, X-ray tube emission, operating currents and linearized focal spot size functions and gradients therefor, determining a calibration state of the X-ray tube, optionally operating the X-ray tube at a first portion of the number of focal spots to determine any offsets for the initial parameters, optionally updating the initial parameters with the offsets, operating the X-ray tube at each of a second portion of the number of focal spots and determining if any of the second portion of focal spots are outside of calibration tolerance limits.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

DETAILED DESCRIPTION OF THE INVENTION

Embodiments of the present disclosure relate to calibration systems and processes for an X-ray tube operated with microsecond X-ray intensity switching. An exemplary X-ray tube and a computed tomography system employing the exemplary calibration system and method are presented.

Figure 1:
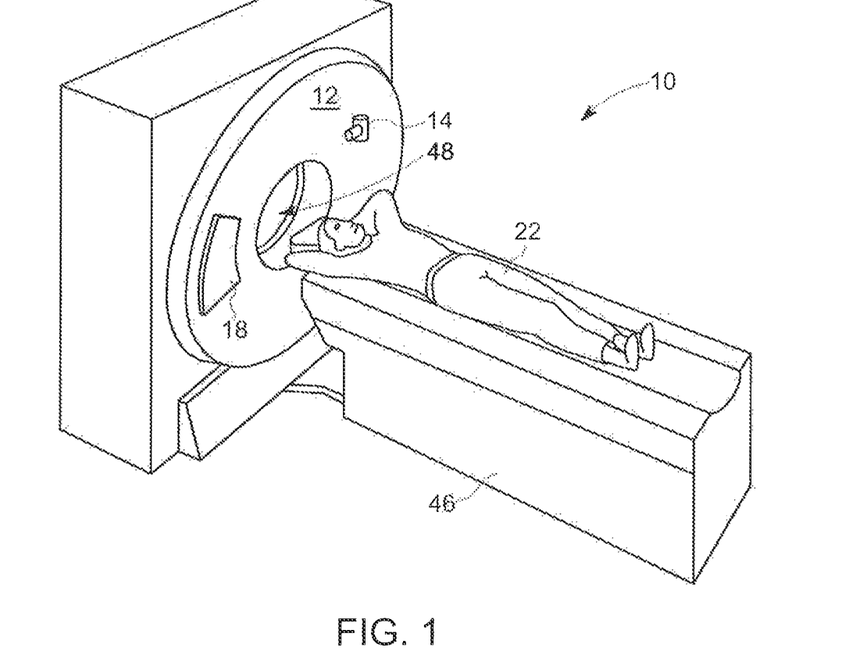
FIG. 1 is an isometric view of a CT imaging system according to an exemplary embodiment of the disclosure.
Figure 2:
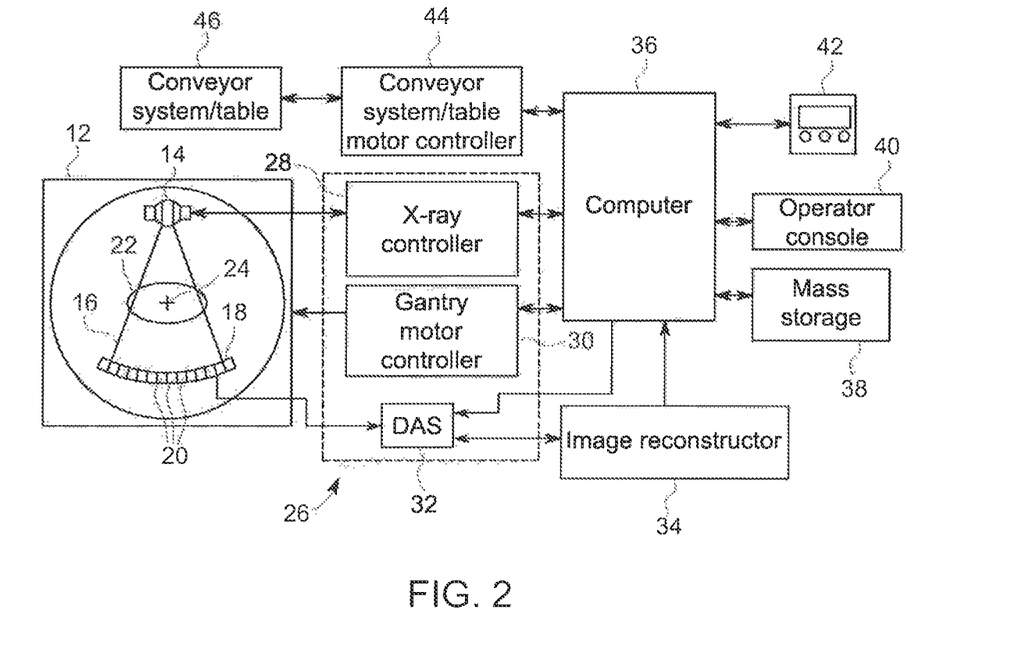
FIG. 2 is a block schematic diagram of the CT imaging system according to an exemplary embodiment of the disclosure.

Referring now to FIGS. 1 and 2, as disclosed in U.S. Pat. No. 8,401,151 entitled X-ray Tube for Microsecond X-ray Intensity Switching, the entirety of which is expressly incorporated herein by reference, a computed tomography (CT) imaging system 10 is illustrated. The CT imaging system 10 includes a gantry 12. The gantry 12 has an X-ray source 14, which typically is an X-ray tube that projects a beam of X-rays 16 towards a detector array 18 positioned opposite the X-ray tube on the gantry 12. In one embodiment, the gantry 12 may have multiple X-ray sources (along the patient theta or patient Z axis) that project beams of X-rays. The detector array 18 is formed by a plurality of detectors 20 which together sense the projected X-rays that pass through an object to be imaged, such as a patient 22. During a scan to acquire X-ray projection data, the gantry 12 and the components mounted thereon rotate about a center of rotation 24. While the CT imaging system 10 described with reference to the medical patient 22, it should be appreciated that the CT imaging system 10 may have applications outside the medical realm. For example, the CT imaging system 10 may be utilized for ascertaining the contents of closed articles, such as luggage, packages, etc., and in search of contraband such as explosives and/or biohazardous materials.

Rotation of the gantry 12 and the operation of the X-ray source 14 are governed by a control mechanism 26 of the CT system 10. The control mechanism 26 includes an X-ray controller 28 that provides power and timing signals to the X-ray source 14 and a gantry motor controller 30 that controls the rotational speed and position of the gantry 12. A data acquisition system (DAS) 32 in the control mechanism 26 samples analog data from the detectors 20 and converts the data to digital signals for subsequent processing. An image reconstructor 34 receives sampled and digitized X-ray data from the DAS 32 and performs high-speed reconstruction. The reconstructed image is applied as an input to a computer 36, which stores the image in an electronic mass storage device, database or memory 38 or subdivision thereof.

Moreover, the computer 36 also receives commands and scanning parameters from an operator via operator console 40 that may have an input device such as a keyboard (not shown in FIGS. 1-2). An associated display 42 allows the operator to observe the reconstructed image and other data from the computer 36. Commands and parameters supplied by the operator are used by the computer 36 to provide control and signal information to the DAS 32, the X-ray controller 28 and the gantry motor controller 30. In addition, the computer 36 operates a table motor controller 44, which controls a motorized table 46 to position the patient 22 and the gantry 12. Particularly, the table 46 moves portions of patient 22 through a gantry opening 48. It may be noted that in certain embodiments, the computer 36 may operate a conveyor system controller 44, which controls a conveyor system 46 to position an object, such as, baggage or luggage and the gantry 12. More particularly, the conveyor system 46 moves the object through the gantry opening 48.

The X-ray source 14 is typically an X-ray tube that includes at least a cathode and an anode. The cathode may be a directly heated cathode or an indirectly heated cathode. Currently, X-ray tubes include an electron source to generate an electron beam and impinge the electron beam on the anode to produce X-rays. These electron sources control a beam current magnitude by changing the current on the filament, and therefore emission temperature of the filament. Unfortunately, these X-ray tubes fail to control electron beam intensity to a view-to-view basis based on scanning requirements, thereby limiting the system imaging options. Accordingly, an exemplary X-ray tube is presented, where the X-ray tube provides microsecond current control during nominal operation, on/off gridding for gating or usage of multiple X-ray sources, 0 percent to 100 percent modulation for improved X-ray images, and dose control or fast voltage switching for generating X-rays of desired intensity resulting in enhanced image quality.

Figure 3:
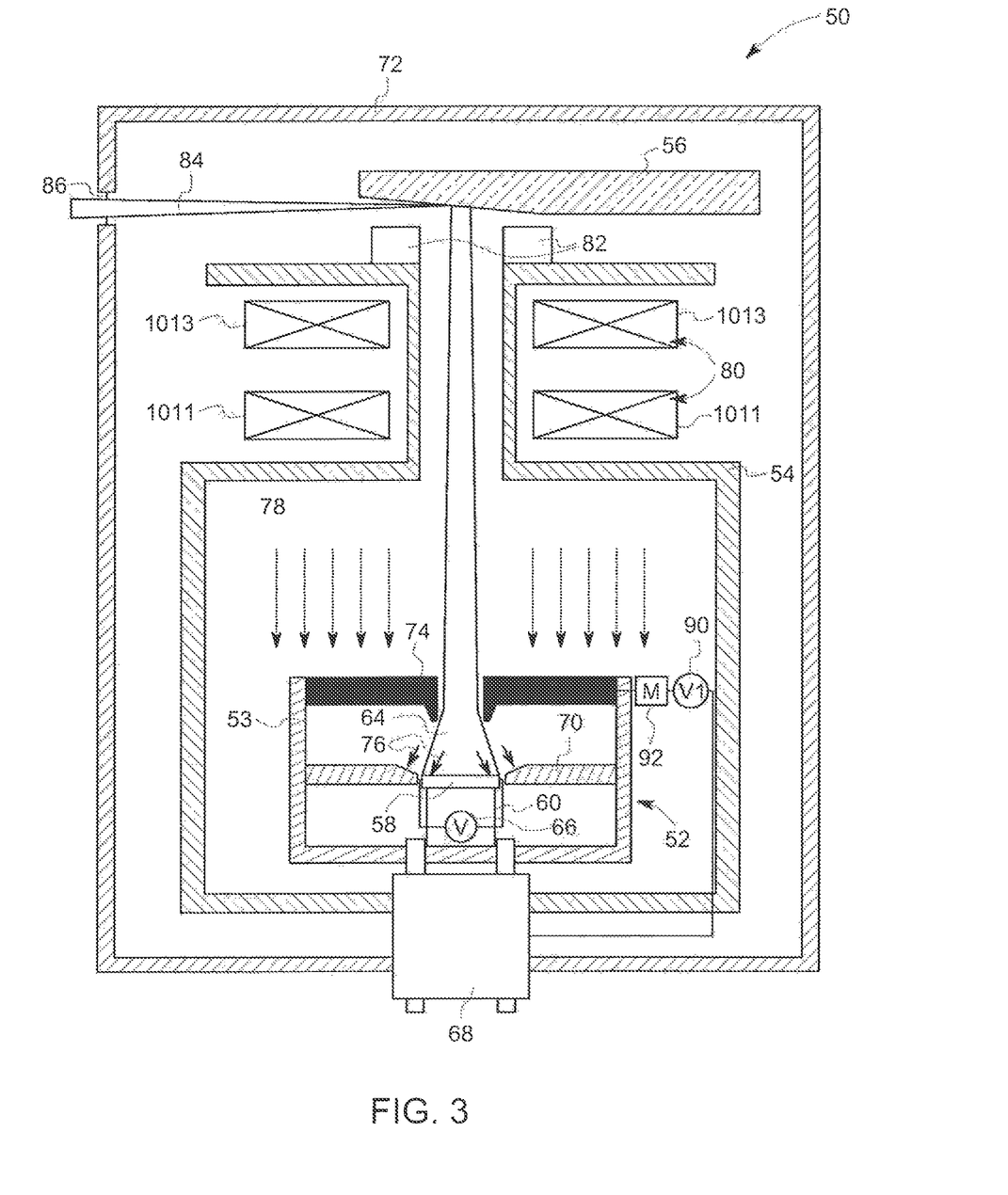
FIG. 3 is a schematic cross-sectional view of an X-ray tube according to an exemplary embodiment of the disclosure.

FIG. 3 is a diagrammatical illustration of an exemplary X-ray tube 50, in accordance with aspects of the present technique. In one embodiment, the X-ray tube 50 may be the X-ray source 14 (see FIGS. 1-2). In the illustrated embodiment, the X-ray tube 50 includes an exemplary injector 52 disposed within a vacuum wall 54. Further, the injector 52 includes an injector wall 53 that encloses various components of the injector 52. In addition, the X-ray tube 50 also includes an anode 56. The anode 56 is typically an X-ray target. The injector 52 and the anode 56 are disposed within an X-ray tube casing 72. In accordance with aspects of the present technique, the injector 52 may include at least one cathode in the form of an emitter 58. In the present example, the cathode, and in particular the emitter 58, may be directly heated. Further, the emitter may be coupled to an emitter support 60, and the emitter support 60 in turn may be coupled to the injector wall 53. The emitter 58 may be heated by passing a large current through the emitter 58. A voltage source 66 may supply this current to the emitter 58. In one embodiment, a current of about 10 amps (A) may be passed through the emitter 58. The emitter 58 may emit an electron beam 64 as a result of being heated by the current supplied by the voltage source 66. As used herein, the term "electron beam" may be used to refer to a stream of electrons that have substantially similar velocities.

The electron beam 64 may be directed towards the target 56 to produce X-rays 84. More particularly, the electron beam 64 may be accelerated from the emitter 58 towards the target 56 by applying a potential difference between the emitter 58 and the target 56. In one embodiment, a high voltage in a range from about 40 kVp to about 150 kVp may be applied via use of a high voltage feedthrough 68 to set up a potential difference between the emitter 58 and the target 56, thereby generating a high voltage main electric field 78. In one embodiment, a high voltage differential of about 140 kVp may be applied between the emitter 58 and the target 56 to accelerate the electrons in the electron beam 64 towards the target 56. It may be noted that in the presently contemplated configuration, the target 56 may be at ground potential. By way of example, the emitter 58 may be at a potential of about −140 kVp and the target 56 may be at ground potential or about zero volts.

In an alternative embodiment, emitter 58 may be maintained at ground potential and the target 56 may be maintained at a positive potential with respect to the emitter 58. By way of example, the target may be at a potential of about 140 kVp and the emitter 58 may be at ground potential or about zero volts.

Moreover, when the electron beam 64 impinges upon the target 56, a large amount of heat is generated in the target 56. Unfortunately, the heat generated in the target 56 may be significant enough to melt the target 56. In accordance with aspects of the present technique, a rotating target may be used to circumvent the problem of heat generation in the target 56. More particularly, in one embodiment, the target 56 may be configured to rotate such that the electron beam 64 striking the target 56 does not cause the target 56 to melt since the electron beam 64 does not strike the target 56 at the same location. In another embodiment, the target 56 may include a stationary target. Furthermore, the target 56 may be made of a material that is capable of withstanding the heat generated by the impact of the electron beam 64. For example, the target 56 may include materials such as, but not limited to, tungsten, molybdenum, or copper.

In the presently contemplated configuration, the emitter 58 is a flat emitter. In an alternative configuration the emitter 58 may be a curved emitter. The curved emitter, which is typically concave in curvature, provides pre-focusing of the electron beam. As used herein, the term "curved emitter" may be used to refer to the emitter that has a curved emission surface. Furthermore, the term "flat emitter" may be used to refer to an emitter that has a flat emission surface. In accordance with aspects of the present technique shaped emitters may also be employed. For example, in one embodiment, various polygonal shaped emitters such as, a square emitter, or a rectangular emitter may be employed. However, other such shaped emitters such as, but not limited to elliptical or circular emitters may also be employed. It may be noted that emitters of different shapes or sizes may be employed based on the application requirements.

In accordance with aspects of the present technique, the emitter 58 may be formed from a low work-function material. More particularly, the emitter 58 may be formed from a material that has a high melting point and is capable of stable electron emission at high temperatures. The low work-function material may include materials such as, but not limited to, tungsten, thoriated tungsten, lanthanum hexaboride, and the like.

With continuing reference to FIG. 3, the injector 52 may include at least one focusing electrode 70. In one embodiment, the at least one focusing electrode 70 may be disposed adjacent to the emitter 58 such that the focusing electrode 70 focuses the electron beam 64 towards the target 56. As used herein, the term "adjacent" means near to in space or position. Further, in one embodiment, the focusing electrode 70 may be maintained at a voltage potential that is less than a voltage potential of the emitter 58. The potential difference between the emitter 58 and focusing electrode 70 prevents electrons generated from the emitter 58 from moving towards the focusing electrode 70. In one embodiment, the focusing electrode 70 may be maintained at a negative potential with respect to that of the emitter 58. The negative potential of the focusing electrode 70 with respect to the emitter 58 focuses the electron beam 64 away from the focusing electrode 70 and thereby facilitates focusing of the electron beam 64 towards the target 56.

In another embodiment, the focusing electrode 70 may be maintained at a voltage potential that is equal to or substantially similar to the voltage potential of the emitter 58. The similar voltage potential of the focusing electrode 70 with respect to the voltage potential of the emitter 58 creates a parallel electron beam by shaping electrostatic fields due to the shape of the focusing electrode 70. The focusing electrode 70 may be maintained at a voltage potential that is equal to or substantially similar to the voltage potential of the emitter 58 via use of a lead (not shown in FIG. 3) that couples the emitter 58 and the focusing electrode 70.

Moreover, in accordance with aspects of the present technique, the injector 52 includes at least one extraction electrode 74 for additionally controlling and focusing the electron beam 64 towards the target 56. In one embodiment, the at least one extraction electrode 74 is located between the target 56 and the emitter 58. Furthermore, in certain embodiments, the extraction electrode 74 may be positively biased via use of a voltage tab (not shown in FIG. 3) for supplying a desired voltage to the extraction electrode 74. In accordance with aspects of the present technique, a bias voltage power supply 90 may supply a voltage to the extraction electrode 74 such that the extraction electrode 74 is maintained at a positive bias voltage with respect to the emitter 58. In one embodiment, the extraction electrode 74 may be divided into a plurality of regions having different voltage potentials to perform focusing or a biased emission from different regions of the emitter 58.

It may be noted that, in an X-ray tube, the energy of an X-ray beam may be controlled via one or more of multiple ways. For instance, the energy of an X-ray beam may be controlled by altering the potential difference (that is acceleration voltage) between the cathode and the anode, or by changing the material of the X-ray target, or by filtering the electron beam. This is generally referred to as "kVp control." As used herein, the term "electron beam current" refers to the flow of electrons per second between the cathode and the anode. Furthermore, an intensity of the X-ray beam is controllable via control of the electron beam current. Such a technique of controlling the intensity is generally referred to as "mA control." As discussed herein, aspects of the present technique provide for control of the electron beam current via use of the extraction electrode 74. It may be noted that, the use of such extraction electrode 74 enables a decoupling of the control of electron emission from the acceleration voltage.

Furthermore, the extraction electrode 74 is configured for microsecond current control. Specifically, the electron beam current may be controlled in the order of microseconds by altering the voltage applied to the extraction electrode 74 in the order of microseconds. It may be noted that the emitter 58 may be treated as an infinite source of electrons. In accordance with aspects of the present technique, electron beam current, which is typically a flow of electrons from the emitter 58 towards the target 56, may be controlled by altering the voltage potential of the extraction electrode 74. Control of the electron beam current will be described in greater detail hereinafter.

With continuing reference to FIG. 3, the extraction electrode 74 may also be biased at a positive voltage with respect to the focusing electrode 70. As an example, if the voltage potential of emitter 58 is about −140 kVp, the voltage potential of the focusing electrode 70 may be maintained at about −140 kVp or less, and the voltage potential of the extraction electrode 74 may be maintained at about −135 kVp for positively biasing the extraction electrode 74 with respect to the emitter 58. In accordance with aspects of the present technique, an electric field 76 is generated between the extraction electrode 74 and the focusing electrode 70 due to a potential difference between the focusing electrode 70 and the extraction electrode 74. The strength of the electric field 76 thus generated may be employed to control the intensity of electron beam 64 generated by the emitter 58 towards the target 56. The intensity of the electron beam 64 striking the target 56 may thus be controlled by the electric field 76. More particularly, the electric field 76 causes the electrons emitted from the emitter 58 to be accelerated towards the target 56. The stronger the electric field 76, the stronger is the acceleration of the electrons from the emitter 58 towards the target 56. Alternatively, the weaker the electric field 76, the lesser is the acceleration of electrons from the emitter 58 towards the target 56.

In addition, altering the bias voltage on the extraction electrode 74 may modify the intensity of the electron beam 64. As previously noted, the bias voltage on the extraction electrode may be altered via use of the voltage tab present on the bias voltage power supply 90. Biasing the extraction electrode 74 more positively with respect to the emitter 58 results in increasing the intensity of the electron beam 64. Alternatively, biasing the extraction electrode 74 less positively with respect to the emitter 58 causes a decrease in the intensity of the electron beam 64. In one embodiment, the electron beam 64 may be shut-off entirely by biasing the extraction electrode 74 negatively with respect to the emitter 58. As previously noted, the bias voltage on the extraction electrode 74 may be supplied via use of the bias voltage power supply 90. Hence, the intensity of the electron beam 64 may be controlled from 0 percent to 100 percent of possible intensity by changing the bias voltage on the extraction electrode 74 via use of the voltage tab present in the bias voltage power supply 90.

Furthermore, voltage shifts of 8 kVp or less may be applied to the extraction electrode 74 to control the intensity of the electron beam 64. In certain embodiments, these voltage shifts may be applied to the extraction electrode 74 via use of a control electronics module 92. The control electronics module 92 changes the voltage applied to the extraction electrode 74 in intervals of 1-15 microseconds to intervals of about at least 150 milliseconds. In one embodiment, the control electronics module 92 may include Si switching technology circuitry to change the voltage applied to the extraction electrode 74. In certain embodiments, where the voltage shifts range beyond 8 kVp, a silicon carbide (SiC) switching technology may be applied. Accordingly, changes in voltage applied to the extraction electrode 74 facilitates changes in intensity of the electron beam 64 in intervals of 1-15 microseconds, for example. This technique of controlling the intensity of the electron beam in the order of microseconds may be referred to as microsecond intensity switching.

Additionally, the exemplary X-ray tube 50 may also include a magnetic assembly 80 for focusing and/or positioning and deflecting the electron beam 64 on the target 56. In one embodiment, the magnetic assembly 80 may be disposed between the injector 52 and the target 56. In one embodiment, the magnetic assembly 80 may include one or more multipole magnets for influencing focusing of the electron beam 64 by creating a magnetic field that shapes the electron beam 64 on the X-ray target 56. The one or more multipole magnets may include one or more quadrupole magnets, one or more dipole magnets, or combinations thereof. As the properties of the electron beam current and voltage change rapidly, the effect of space charge and electrostatic focusing in the injector will change accordingly. In order to maintain a stable focal spot size, or quickly modify focal spot size according to system requirements, the magnetic assembly 80 provides a magnetic field having a performance controllable from steady-state to a sub-30 microsecond time scale for a wide range of focal spot sizes. This provides protection of the X-ray source system, as well as achieving CT system performance requirements. Additionally, the magnetic assembly 80 may include one or more dipole magnets for deflection and positioning of the electron beam 64 at a desired location on the X-ray target 56. The electron beam 64 that has been focused and positioned impinges upon the target 56 to generate the X-rays 84. The X-rays 84 generated by collision of the electron beam 64 with the target 56 may be directed from the X-ray tube 50 through an opening in the X-ray tube casing 72, which may be generally referred to as an X-ray window 86, towards an object (not shown in FIG. 3).

With continuing reference to FIG. 3, the electrons in the electron beam 64 may get backscattered after striking the target 56. Therefore, the exemplary X-ray tube 50 may include an electron collector 82 for collecting electrons that are backscattered from the target 56. In accordance with aspects of the present technique, the electron collector 82 may be maintained at a ground potential. In an alternative embodiment, the electron collector 82 may be maintained at a potential that is substantially similar to the potential of the target 56. Further, in one embodiment, the electron collector 82 may be located adjacent to the target 56 to collect the electrons backscattered from the target 56. In another embodiment, the electron collector 82 may be located between the extraction electrode 74 and the target 56, close to the target 56. In addition, the electron collector 82 may be formed from a refractory material, such as, but not limited to, molybdenum. Furthermore, in one embodiment, the electron collector 82 may be formed from copper. In another embodiment, the electron collector 82 may be formed from a combination of a refractory metal and copper.

Furthermore, it may be noted that the exemplary X-ray tube 50 may also include one or more ion management electrodes (not shown in FIG. 3) either to repel or to attract positive ions that may be produced due to collision of electrons in the electron beam 64 with the target 56 and with the residual gas. A positive ion barrier for example is generally placed along the electron beam path and prevents the positive ions from striking various components in the X-ray tube 50, thereby preventing damage to the components in the X-ray tube 50, particularly components that are part of the injector 52.

Table 1, below, is an overview of the aspects and associated processes for calibrating the X-ray source or X-ray tube 14 within the imaging system 10. The first aspect/step (Sweeper) is employed after initial manufacture of the X-ray tube 14 and generates the necessary magnet current seed values and sensitivity/gradient coefficients that are required for any later calibration of the X-ray tube 14 needed in the field. The second aspect/step (Calibrator) can be employed or performed at any later time in the field with the X-ray tube 14 installed in a system 10 to correct for any drift in X-ray tube performance over time. The second aspect/step uses the seed values produced in the Sweeper or the magnet currents from the latest most recent calibration as a starting point and then calibrates the X-ray tube 14 using the sensitivities from provided by the Sweeper in aspect/step 1. The last aspect/step (Tabulator) provides an interpolation algorithm to compute magnet calibration values for any intermediate X-ray tube emission values that were not calibrated in the prior aspects/steps.

TABLE 1

| Calibration System Aspects | |
|---|---|
| Focal Spot Calibration Software Modules | Function |
| Sweeper | Find QC, QT seed values and gradients for all focal spots across kVp/mA space. Sweeper seed and gradient data passed to Calibrator fir subsequent calibration processes |
| Calibrator | Iterative, gradient-based process that refines QC, QT to within the calibration tolerance for MTF at 50% intensity for all focal spots. Can be performed during manufacturing, upon initial installation in CT system and when necessary after installation. Data from calibrator stored in X-ray tube interface, magnet control board and/or CT system for import to tabulator and back-up |
| Tabulator | Interpolates data from Calibrator and applies any required offsets to create patient look up table for patient scan |

Figure 4A:
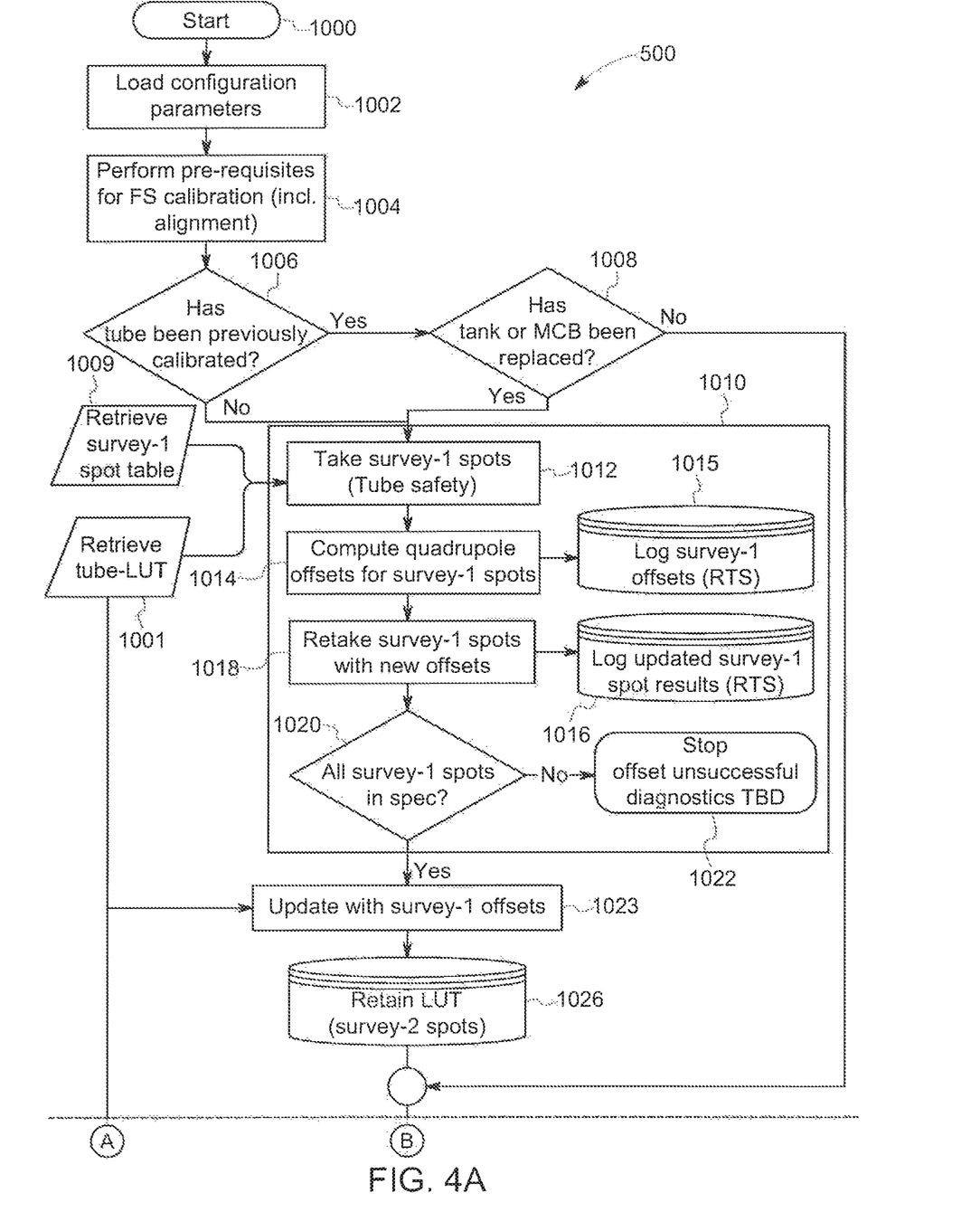
FIGS. 4A-4B are a flowchart of the calibration system and process according to an exemplary embodiment of the disclosure.
Figure 4B:
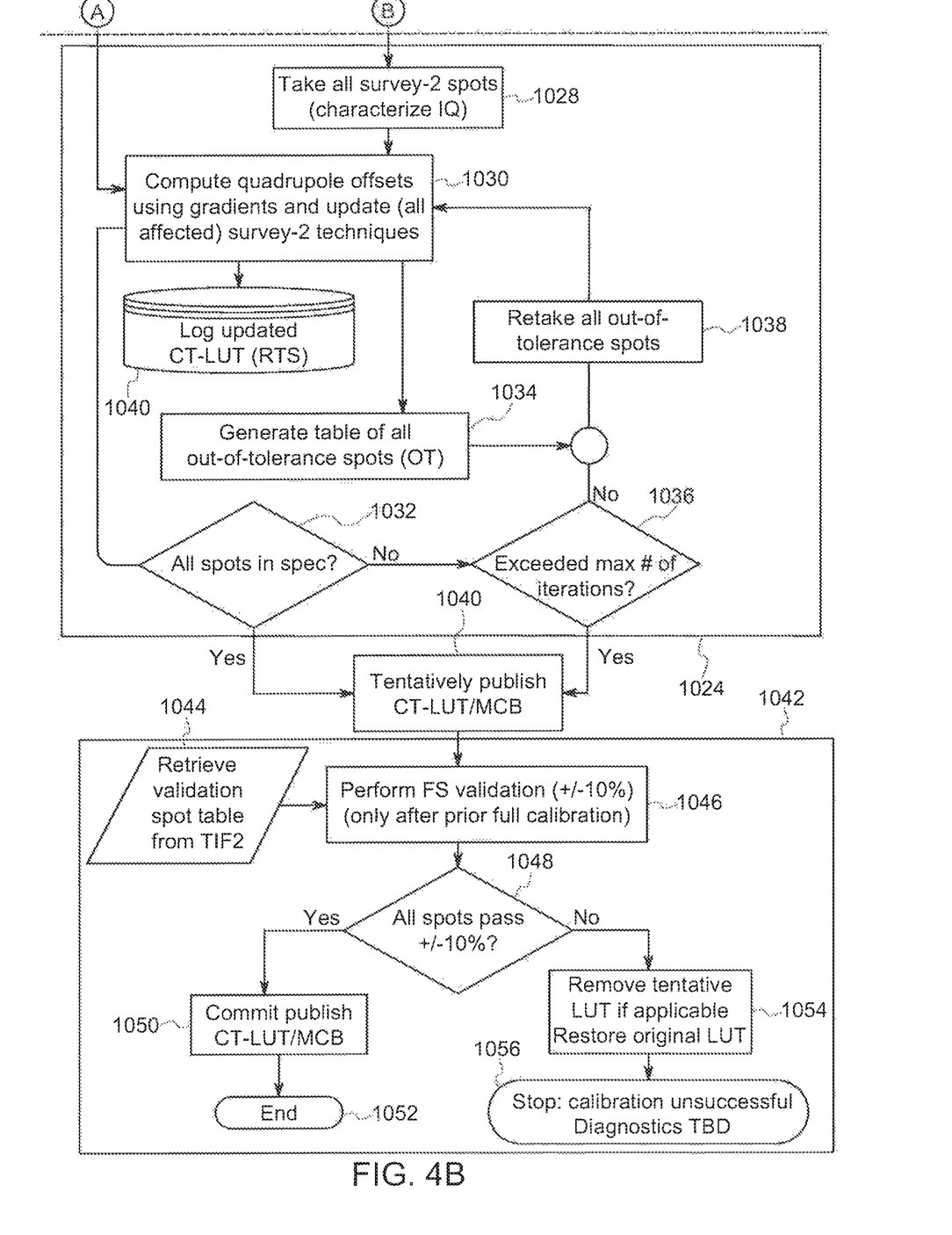
Figure 5:
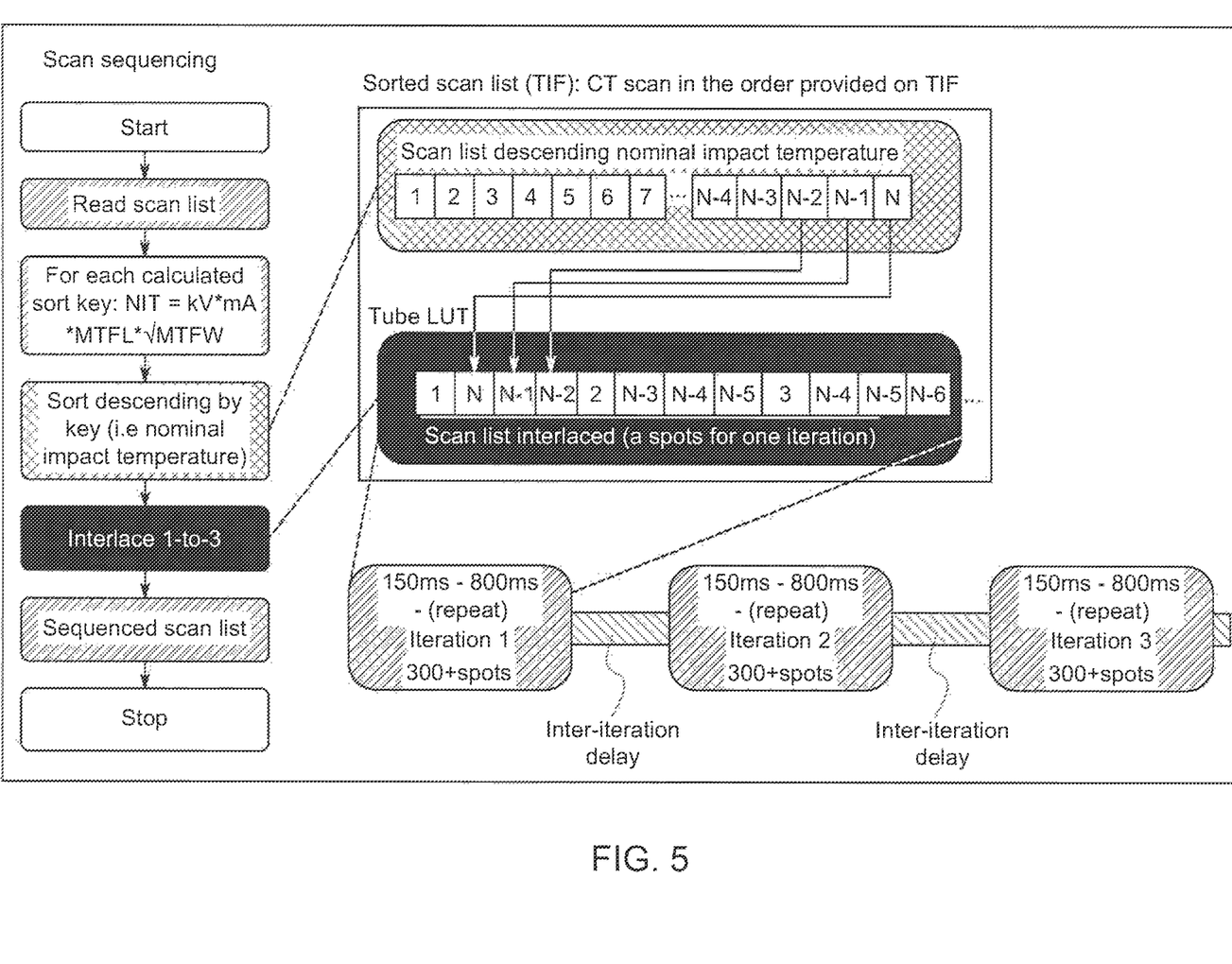
FIG. 5 is a flowchart of a scan sequencing system and process employed with the calibration system of FIGS. 4A-4B according to an exemplary embodiment of the disclosure.

FIGS. 4A, 4B and 5 show an exemplary block diagram of a process 500 for calibrating the X-ray source or X-ray tube 14 within the imaging system. Initially, from start block 1000 where the calibration process is initiated manually or automatically, such as in response to the expiration of a predetermined time period for operation of the source 14, the system 10 moves to block 1002 to access the configuration parameters for the calibration procedure upon connection of the source 14 to the system 10. The Configuration parameters are stored in the form of an X-ray tube look up table (LUT) 1001 that is found in a suitable electronic storage medium disposed on an X-ray tube interface (TIF) board (not shown) formed as part of the source 14 and operably interconnected to the system 10 upon engagement of the source 14 to the system 10, thereby enabling access to the X-ray tube LUT 1001 by the system 10. These parameters can include, but are not limited to a determination of the upper and lower emission values for the source 14 to be utilized in the scan techniques for the various calibration steps on the given focal spot sizes to be calibrated, as well as the nominal values, target values, safety focal spot tolerances, calibration tolerances and system validation tolerances for the focal spots being calibrated within specified source emission and voltage ranges and the magnet settings i.e., QC/QT, that are determined during initial testing of the source 14 that can occur during or immediately after initial production or manufacturing of the X-ray source 14 for selected focal spots. In block 1002, the system 10 accesses these parameters and determines if the scan(s) would cause the emission from the source 14 to fall outside of the minimum and maximum emission ranges set for the scan(s) at which point the system 10 stop the calibration procedure set up. In block 1002, if the emissions for the scan techniques fall within the minimum and maximum values, the system 10 can additionally locate an index for emission bracketing techniques and compute the linear interpolation for the magnetic currents to be used for the scans.

Subsequently, the system 10 moves to block 1004 in order to perform the various pre-requisite set up procedures for the calibration of the source 14. These pre-requisites include, but are not limited to confirming the emitter and/or extractor calibration and source alignment are complete, performing a number of air scans at various voltages, current, and/or focal spot sizes defined within the X-ray tube LUT 1001 on the X-ray tube interface (TIF) board, and employing preset adaptive source warmup or cooldown procedures to ensure the source 14 is within set cathode and target track temperature requirements located within the X-ray tube LUT 1001 on the TIF board. These temperature requirements for the cathode and target track in the source 14 are controlled by a source protection algorithm (SPA) stored on the X-ray tube LUT 1001 and executed by the system 10 during the entire calibration procedure to protect the source 14 and ensure stable MTF performance during the calibration process.

After the prerequisites for the calibration procedure have been met in block 1004, the system 10 proceeds to block 1006 to determine if the source 14 has recently been calibrated and/or block 1008 to determine if a system component (not shown) related to the proper operation of the source 14, such as the high voltage tank or magnet control board, among others, has recently been replaced. If the source 14 was recently calibrated and no components have been replaced, the system 10 proceeds with a more detailed, second stage calibration process 1024, to be described.

However, if either the source 14 has not been recently calibrated or a related component of the system 10 has recently been replaced, as shown in the exemplary embodiment of FIG. 4A the system 10 moves to block 1010 to perform a preliminary, first stage calibration process. In the first stage 1010, a limited number of scans are performed with the source 14 to detect any shift or current offset in the focusing elements 80, such as due to the source 14 being operated with a different MCB than used during initial testing, that may generate high impact temperature focal spots exceeding X-ray tube limitations. The list of scan techniques 1009 for the first stage 1010 are stored in the X-ray tube LUT 1001 and include data on the X-ray tube voltage (kVp), X-ray tube emission (mA) and size of the focal spot (fs) for each scan, as well as the current values for the focusing elements 80 to be utilized. In an exemplary embodiment, the focusing elements 80 are quadrupole magnets, paired as QC 1011 and QT magnets 1013 (FIG. 3), respectively, and the current values for the focusing elements 80 are provided as values QC, QT for the QC magnets 1011 and the QT magnets 1013.

Along with the scan technique parameters, the X-ray tube LUT 1001 includes various gradient coefficients W0 (lp/cm), W1 (lp/cm*mA), W2 (lp/cm*mA), L0 (lp/cm), L1 (lp/cm*mA) and L2 (lp/cm*mA) that are utilized in linearized focal spot size functions, such as MTF equations standardized at 50% intensity for the width and length values, i.e., MTFW (lp/cm) and MTFL (lp/cm), of the focal spots for each scan technique. The data associated with each scan technique stored in the X-ray tube LUT is determined during the initial testing/calibration of the source 14 and stored in the X-ray tube LUT to be accessed by the system 10 during the calibration process, e.g., data generated during manufacturing of the source at nominal alignment, or zero deflection currents in the dipoles.

Once the scan techniques for the first stage 1010 have been determined from the X-ray tube LUT 1001, which can be as few as six (6) in an exemplary embodiment, the system 10 proceeds in block 1012 to operate the source 14 to perform those scans and obtain actual or measured MTFW and MTFL values from each scan. In block 1014 this data along with the gradient coefficients for each is utilized in the following equations to compute a quadrupole offset $QP_{offset}$ that minimizes the following equations:

$$MIN((-MTFW-MTFW\_spec)^2+(MTFL-MTFL\_spec)^2(QP_{offset}))$$

where $MTFW=MTFW\_measured+QP_{offset}$ (which is a function of $W1,W2,\ldots$)

and $MTFL=MTFL\_measured+QP_{offset}$ (which is a function of $L1,L2,\ldots$)

The minimum sum is evaluated within a range of −10 mA to +10 mA, for example. The current offset that minimizes the sum ($QP_{min}$) is then added to all QC and QT currents in the X-ray tube LUT 1001 according to the following equations:

$$QC_{new}=QC_{old}+QP_{offset}$$

$$QT_{new}=QT_{old}+QP_{offset}$$

And the resulting values for QC and QT associated with each scan technique are recorded, such as temporarily in computer memory 38, by the system 1000 in block 1015.

Once the QC and QT values are updated, the first stage scan techniques are re-run in block 1016, with the results recorded, such as temporarily in computer memory 38, by the system 1000 in block 1018. The results for the focal spots obtained in these re-run scans are compared with the tolerances for the scan techniques, also stored within the X-ray tube LUT 1001 in block 1020. If the focal spots are found to be outside of the tolerance ranges, in block 1022 the system 1000 provides an alert concerning the error and stops the calibration process until a suitable intervention has been performed on the system 10.

Alternatively, if the measured focal spots fall within the stored tolerances, the system 1000 updates all of the stored QC and QT values for all scan techniques in the X-ray tube LUT 1001 with the offset in block 1023, and then proceeds to block 1024 to perform a more detailed, second stage calibration procedure. This second stage procedure is performed similarly to the first stage procedure in block 1010 but with the addition of multiple scan techniques associated with techniques associated with approximately three hundred (300) focal spots that establish a complete characterization of all focal spot sizes over the full performance range of the source 14.

In the second stage calibration 1024 (FIG. 4B), the system 1000 in block 1026 initially accesses the X-ray tube LUT 1001 to locate the values of focal spot size (fs), X-ray tube voltage (kVp), X-ray tube emission (mA), QC, QT, $MFTW_{goal}$, $MFTL_{goal}$, W0, W1, W2, L0, L1 and L2 for each scan technique, which is also the step to which the overall process proceeds in the event that a determination is made in blocks 1006 and 1008 that the source 14 has been recently calibrated and that no components of the system 10 have recently been replaced. In addition, all of the information regarding the latest calibration is copied into the storage 38, such as in a CT look up table (CT-LUT) on the system 10 to provide an additional record of the last calibration of the source 14.

Initially, in block 1028 the system 1000 performs each scan stored in the X-ray tube LUT 1001 for the second stage calibration process using the stored values. For each scan, the data on the focal spot measurement provides values for MTFW and MTFL. In block 1030, these values can be used to provide quadrupole offsets in the following equations to solve for QC and QT:

$$MTFW=W0+QC*W1+QT*W2$$

$$MTFL=L0+QC*L1+QT*L2$$

These equations (MTF linearization) can be solved to provide the quadrupole currents QC, QT that yield MTFW and MTFL. Likewise, the quadrupole currents for the goal MTF ($MFTW_{goal}$, $MFTL_{goal}$) can be obtained as $QC_{goal}$, $QT_{goal}$. The predicted change in the quadrupole current to focus the actual focal spot within the tolerances provided is therefore:

$$dQC=QC-QC_{goal}$$

$$dQT=QT-QT_{goal}$$

After transforming the linear equations for MTFW and MTFL, the quadrupole current changes can be calculated as follows:

$$dw=MTFW_{goal}-MTFW$$

$$dl=MTFL_{goal}-MTFL$$

$$dQT=(L1*dw-W1*dl)/(L1*W2-W1*L2)$$

$$dQC=dw/W1-W2/W*dQT$$

Thus, for any given MTF (MTFW, MTFL) measurement, the measurement returns values for the magnet current change (dQC, dQT) to bring the focal spot within the required tolerances. Any initially out of tolerance focal spots determined by the scan (block 1032) are stored in an internal list within the X-ray tube LUT 1001 (block 1034). If the number of scans performed for calibration of an out of tolerance focal spot on the list have not exceeded the maximum number of scans/iterations allowed (block 1036), the scan for the focal spot is retaken (block 1038) until the focal spot with within tolerances or the number of iterations for the calibration scan has been exceeded. This process employed in blocks 1030, 1032, 1034, 1036 and 1038 is iterative due to the existing non-linearities and measurement uncertainties, but normally converges within a small number of iteration steps, such as less than five (5) steps. For each iteration, the X-ray tube LUT 1001 employs a convergence tolerance of 2% of the goal value, as convergence is only possible within the MTF measurement error and the MTF variability that is influenced by various factors, e.g., the temperature of the source 14, such that any scan results reaching this threshold will result in stoppage of the scans for that focal spot. Further, the X-ray tube LUT 1001 can contain a maximum for the number of iterations that will be performed for any focal spot measurement.

To avoid any oscillation around the result, a common factor scaled can be employed to dampen a calculated current step (dQC, dQT) if the preceding measurement overshot the MTF goal in width and/or in length. In employing the dampening, the following equation can be utilized:

$$dQC=scaleDQ*dQC$$

$$dQT=scaleDQ*dQT$$

Further, in block 1030, to avoid inadvertent large changes to the focal spot during calibration a limit can be applied to the magnet steps dQC,dQT after dampening. In doing so, the magnet step is limited to the maximum step allowable either for QC or QT while the other is adjusted according to its sensitivity. This ensures that a new, safe calibration point is generated that moves the calibration in the proper direction towards the solution.

After the initial scan and necessary subsequent iterations thereof have been performed, the updated calibration information is copied over the CT-LUT present within the storage 38 on the system 10 in block 1040. Further, any out of tolerance focal spots that have exceeded the maximum number of iterations can be compared with system validation tolerances, as even if individual focal spot scan techniques did not converge during the iterations performed, the focal spots used for system validation may still fall within system tolerance specifications.

In the situation where the second stage calibration fail to converge or diverges, the sum of squares, i.e., $\Sigma(i)=dw(i)^2+-dl(i)^2$ is calculated for each scan/iteration performed for a particular focal spot and the result with the minimum sum is selected for storage in the X-ray tube LUT 1001.

During the process provided by blocks 1030-1038, the system 10 employs a scan sequencing technique to avoid violating thermal limitation for the source 14. The sequencing ensures the calibration process is not inadvertently interrupted by the source protection algorithm to enable quality calibration results to be obtained.

To perform the scan sequencing using the sequencing rules stored in the X-ray tube LUT 1001, as illustrated in the exemplary embodiment of FIG. 5, initially the system 10 initially orders all of the scans to be performed in the second stage calibration in order of decreasing expected focal spot temperature. With this list, the highest power scan to be performed is ordered first, with the next three scans performed being the three lowest power scans. This process is repeated by grouping the next highest power scan with the next three lowest power scans, until all initial scans to be performed in the second stage calibration are ordered into group of four scans, with the first scan being a high-power scan followed by three successive low-power scans. In one exemplary embodiment, each scan performed has a duration of between 10 ms to 500 ms, and can be approximately 150 ms, with a delay of between 500 ms to 5000 ms, and can be 800 ms between successive scans. In this manner the heat generated by the initial high-power scan is allowed to dissipate during performance of the low-power scan prior to any subsequent high-power scan being performed, thereby maintaining the temperature within the source 14 at levels within the tolerances for the source protection algorithm.

Additionally, because certain focal spots will require subsequent iterations, the scan sequencing algorithm also accommodates for multiple sets or iterations of scan to be performed with the source 14 by the system 10. To provide the necessary temperature control, the scan sequencing algorithm employs an inter-iteration delay before beginning a subsequent sequence of scans. This inter-iteration delay allows the source 14 to cool effectively, and in one exemplary embodiment is a time period of approximately fifteen (15) minutes between scan iterations.

Further, as during the second stage calibration process certain scan techniques for particular focal points will reach convergence prior to others, in order to accommodate for those scans that do not require any further iterations and will not be re-executed, an empty scan, the scan sequencing algorithm will initially determine if the empty scan is a high or low temperature impact scan, i.e., if the scan would be the first high-power scan of the four scan grouping, or one of the three low-power scan of the grouping. If the empty scan is the high-power scan, the scan sequencing algorithm replaces the empty exposure/scan with a delay of 0 ms, as no delay is required due to the absence of the high-power scan. Alternatively, if the empty scan is a low-power scan, the scan sequencing algorithm replaces the empty scan with an exposure time of 0 ms, but maintains the interscan delay of 800 ms.

After the second stage calibration process 1024 has been completed, i.e., all focal spots are determined to be within tolerances or have exceeded the maximum number of iterations for the second stage calibration process, the system 1000 proceeds to block 1040 to record the second stage calibration data within the CT-LUT on the system. This data can subsequently be utilized by the system 10 during a patient scan.

Further, with all the focal spots within the second stage calibration having been scanned, the system 10 can move to a focal spot validation process 1042. The focal spot validation process 1042 is similar to the second stage calibration process 1024, but uses only a subset of the focal spots scanned in the second stage, i.e., a validation focal spot list, stored in the X-ray tube LUT 1001. This focal spot list provides the system 10 with the focal spots, which may or may not correspond to techniques utilized in the second stage calibration process 1024, for direct comparison with the system validation tolerances also stored within the X-ray tube LUT 1001. To do so, in block 1044, the system 10 retrieves validation focal spot table/list. In one exemplary embodiment, the validation focal spots/techniques corresponding to second stage calibration results stored within the CT-LUT on the system 10 for the focal spots listed in the validation table results and the scan results for any other techniques performed according to the validation focal spots/techniques are compared with the validation focal spot tolerances in block 1046 to determine if the results for each of the focal spots fall within the validation tolerance limits. From block 1048, if the results do all fall within tolerance, the system 10 overwrites the CT-LUT with the results from the second stage calibration in block 1050 and the overall calibration process ends in block 1052. Alternatively, if one or more of the focal spots do not fall within the specified validation tolerances, in block 1054 the system 10 removes the second stage calibration results from the CT-LUT and restores the original results, and provides an alert regarding the calibration failure and optionally required maintenance for the system 10 and our source 14 in block 1056.

Figure 6:
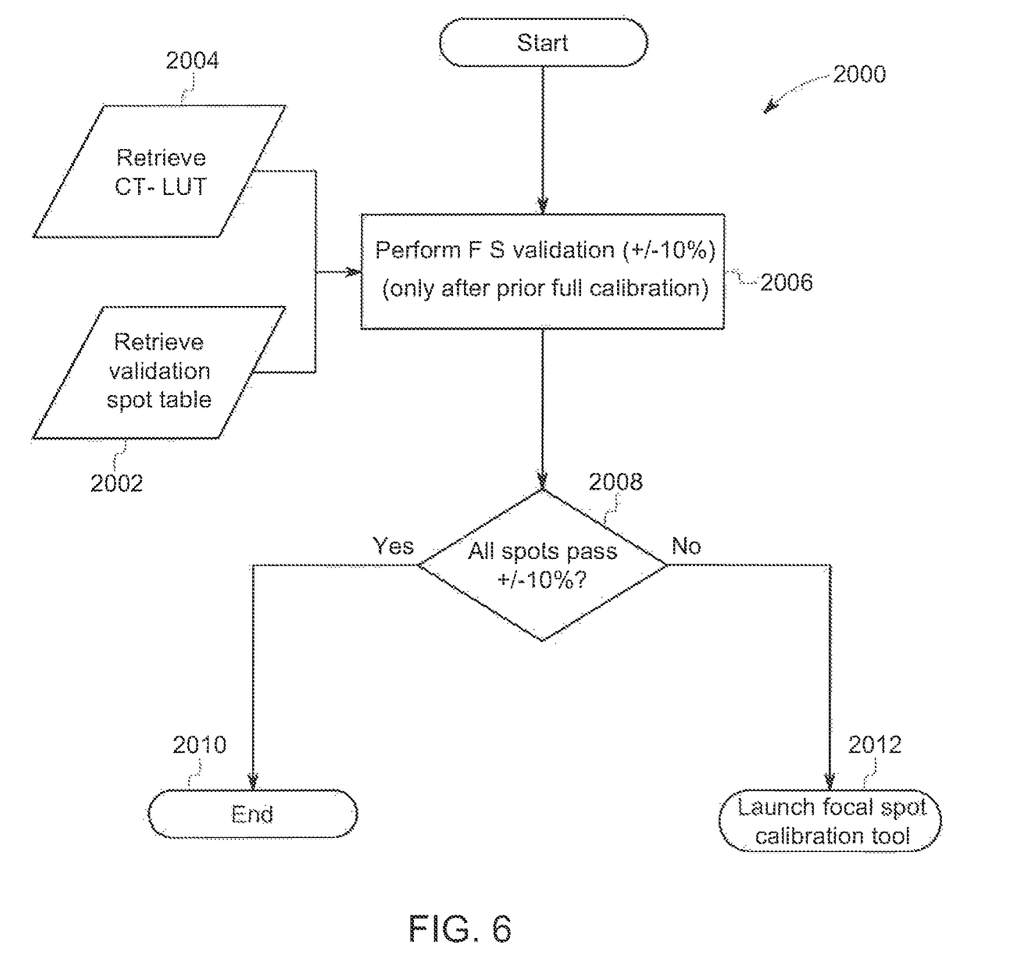
FIG. 6 is a flowchart of a focal spot validation system and process according to an exemplary embodiment of the disclosure.

Further, separate from the overall calibration process 500 in FIGS. 4A-4B, in FIG. 6 an exemplary embodiment of a standalone focal spot validation process 2000 is illustrated. This process 2000 is utilized as a recurring check on the focal spot stability of the source 14 after the source 14 has undergone the complete calibration process 500 and when no other components of the system 10, e.g., the MCB, have been replaced. The validation process 2000 from start 2001 initially retrieves the validation focal spot table or list from the X-ray tube LUT 1001 in block 2002 and the corresponding second stage calibration results for those focal spots from the CT-LUT in block 2004. Similar to the validation process 1042, the system 10 in block 2006 then compares the results to the validation tolerances stored in the X-ray tube LUT 1001 to determine if the results for each of the focal spots fall within the validation tolerance limits. From block 2008, if the results do all fall within tolerance, the validation process ends in block 2010. Alternatively, if one or more of the focal spots do not fall within the specified validation tolerances, in block 2012 the system 10 proceed to initiate the complete calibration process 500, or alternatively provides an indication that the process 500 needs to be initiated.

The written description uses examples to disclose the invention, including the best mode, and enables any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method for the calibration of an X-ray tube comprising the steps of:
   providing original parameters of operation for a first number of focal spots, the original parameters including values for X-ray tube voltage, X-ray tube emission, operating currents and linearized focal spot size functions and gradients therefor;
   operating the X-ray tube at the original parameters;
   determining values for any offsets in the original parameters; and
   updating the original parameters to provide updated parameters for the first number of focal spots, the updated parameters including updated X-ray tube emission.

2. The method of claim 1 wherein X-ray tube includes magnetic focusing elements and wherein the original parameters include operating currents for the magnetic focusing elements.

3. The method of claim 2 wherein the offsets include a global magnet offset current value.

4. The method of claim 3 wherein the original parameters of operation are generated during production of the X-ray tube.

5. A method of calibrating an X-ray tube including magnetic focusing elements, the method comprising the steps of:
providing initial parameters of operation for the X-ray tube at a number of focal spots, the initial parameters including values for X-ray tube voltage, X-ray tube emission, operating currents and linearized focal spot size functions and gradients therefor;
determining a calibration state of the X-ray tube;
optionally operating the X-ray tube at a first portion of the number of focal spots to determine any offsets for the initial parameters;
optionally updating the initial parameters with the offsets;
operating the X-ray tube at each of a second portion of the number of focal spots; and
determining if any of the second portion of focal spots are outside of calibration tolerance limits.

6. The method of claim 5 wherein step of determining if any of the focal spots are outside of calibration tolerance limits comprises:
comparing a measured focal spot value with a goal focal spot value;
determining the difference between the measured focal spot value and the goal focal spot value;
optionally altering the operational current values for the focal spot;
optionally re-operating the X-ray tube at the altered operational current values; and
optionally comparing a re-measured focal spot value with the goal focal spot value.

7. The method of claim 6 wherein the steps of altering the operational current values, re-operating the X-ray tube at the altered operational current values and comparing a re-measured focal spot value with the goal focal spot value are performed a maximum number of iterations.

8. The method of claim 6 further comprising the step of determining if the measured focal spot values fall within validation tolerances.

9. The method of claim 8 wherein the calibration tolerances are different than the validation tolerances.

10. The method of claim 5 wherein the step of operating the X-ray tube at each of the second portion of focal spots comprises ordering the operations of the X-ray tube in a sequence to maintain a temperature of the X-ray tube within limits of an X-ray tube protection algorithm.

11. The method of claim 10 wherein the ordering of the operations of the X-ray tube comprises:
performing a high-power operation of the X-ray tube; and
performing at least one low-power operation of the X-ray tube.

12. The method of claim 11 wherein the ordering of the operations of the X-ray tube comprises performing grouping of operations of the X-ray tube including a high-power operation of the X-ray tube and a consecutive number of low-power operations of the X-ray tube.

13. The method of claim 11 further comprising providing a delay between each operation of the X-ray tube.

14. The method of claim 11 further comprising providing a delay between each grouping of high-power and low-power operations of the X-ray tubes.

15. The method of claim 10 wherein the ordering of operations of the X-ray tube comprises:
ordering all proposed operations of the X-ray tube from highest power to lowest power;
grouping the highest power operation with a number of the lowest power operations; and
grouping lower high-power operations with numbers of higher low-power operations throughout the ordering of all X-ray tube operations.

16. A system for the calibration of an X-ray tube, the system comprising:
an imaging system having a control mechanism, a computer and an electronic storage device operably connected to one another; and
an X-ray tube connected to the imaging system, wherein the computer is configured to:
access original parameters of operation on the X-ray tube for a first number of focal spots, the original parameters including values for X-ray tube voltage, X-ray tube emission, operating currents and linearized focal spot size functions and gradients therefor;
operating the X-ray tube at the original parameters;
determining values for any offsets in the original parameters; and
updating the original parameters to provide updated parameters for the first number of focal spots, the updated parameters including updated X-ray tube emission.

17. A system for the calibration of an X-ray tube, the system comprising:
an imaging system having a control mechanism, a computer and an electronic storage device operably connected to one another; and
an X-ray tube connected to the imaging system, wherein the computer is configured to:
access initial parameters of operation for the X-ray tube at a number of focal spots, the initial parameters including values for X-ray tube voltage, X-ray tube emission, operating currents and linearized focal spot size functions and gradients therefor;
determining a calibration state of the X-ray tube;
optionally operating the X-ray tube at a first portion of the number of focal spots to determine any offsets for the initial parameters;
optionally updating the initial parameters with the offsets;
operating the X-ray tube at each of a second portion of the number of focal spots; and
determining if any of the second portion of focal spots are outside of calibration tolerance limits.

18. The system of claim 17 wherein operating the X-ray tube at each of the second portion of focal spots comprises ordering the operations of the X-ray tube in a sequence to maintain a temperature of the X-ray tube within limits of an X-ray tube protection algorithm.

19. The system of claim 18 wherein the ordering of operations of the X-ray tube comprises:
ordering all proposed operations of the X-ray tube from highest power to lowest power;
grouping the highest power operation with a number of the lowest power operations; and
grouping lower high-power operations with numbers of higher low-power operations throughout the ordering of all X-ray tube operations.

* * * * *